(12) United States Patent
Au (10) Patent No.: US 12,108,997 B2
(45) Date of Patent: Oct. 8, 2024

(54) SYSTEM WITH GUIDES AND TOOLS OF DIFFERENT FLEXIBILITY

(71) Applicant: Intuitive Surgical Operations, Inc., Sunnyvale, CA (US)

(72) Inventor: Samuel Kwok Wai Au, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 830 days.

(21) Appl. No.: 17/165,245

(22) Filed: Feb. 2, 2021

(65) Prior Publication Data
US 2021/0228293 A1  Jul. 29, 2021

Related U.S. Application Data (63) Continuation of application No. 15/509,062, filed as application No. PCT/US2015/048254 on Sep. 3, 2015, now Pat. No. 10,939,972.
(Continued)

(51) Int. Cl.
*A61B 34/32* (2016.01)
*A61B 10/02* (2006.01)
(Continued)

(52) U.S. Cl.
CPC .......... *A61B 34/32* (2016.02); *A61B 10/0233* (2013.01); *A61B 34/20* (2016.02);
(Continued)

(58) Field of Classification Search
CPC ......... A61B 34/20; A61B 34/30; A61B 34/32; A61B 2090/306; A61B 2090/3614;
(Continued)

(56) References Cited

U.S. PATENT DOCUMENTS 3,500,820 A   3/1970   Almen et al.
7,720,322 B2  5/2010   Prisco et al.
(Continued)

FOREIGN PATENT DOCUMENTS

EP   2489394 A1    8/2012
JP   2007528256 A  10/2007
(Continued)

OTHER PUBLICATIONS

Extended European Search Report for Application No. EP22206477.6, mailed on Jan. 9, 2023, 05 pages.
(Continued)

*Primary Examiner* — David J. McCrosky
(74) *Attorney, Agent, or Firm* — Haynes & Boone, LLP (57) ABSTRACT

A system includes an actuator couplable to a flexible guide tube, a processor, and memory. The actuator is configured to move the flexible guide tube. The memory stores instructions that, when executed by the processor, cause the system to: identify at least one factor associated with insertion or removal of a tool configured to be inserted through or removed from the flexible guide tube; identify, in a first configuration of the flexible guide tube and based on the at least one factor, a section of the flexible guide tube having a bend that the tool cannot traverse; inform a user that the first configuration includes the section having the bend; and command the actuator to move the flexible guide tube to a second configuration. A distal portion of the flexible guide tube is disposed adjacent a target site in the first configuration. The second configuration does not include the bend.

20 Claims, 4 Drawing Sheets

Related U.S. Application Data (60) Provisional application No. 62/048,210, filed on Sep. 9, 2014.

(51) Int. Cl.
  *A61B 34/20* (2016.01)
  *A61B 34/30* (2016.01)
  *A61B 90/00* (2016.01)
  *A61B 90/30* (2016.01)
  *A61M 25/01* (2006.01)
  *B25J 9/16* (2006.01)

(52) U.S. Cl.
  CPC ......... *A61B 34/30* (2016.02); *A61M 25/0113* (2013.01); *A61M 25/0116* (2013.01); *B25J 9/161* (2013.01); *B25J 9/1689* (2013.01); *A61B 2034/2061* (2016.02); *A61B 2034/301* (2016.02); *A61B 2034/303* (2016.02); *A61B 2034/306* (2016.02); *A61B 2090/306* (2016.02); *A61B 2090/3614* (2016.02); *A61M 2025/0166* (2013.01)

(58) Field of Classification Search
  CPC ......... A61B 2034/2061; A61B 2034/301–306; A61B 1/005; A61B 1/0051; A61B 1/0052; A61B 1/0053; A61B 1/0055; A61B 1/0056; A61B 1/0057; A61B 1/0058; A61B 1/008; A61B 1/01; A61B 1/00147–0016; A61B 17/3403; A61B 2017/3405–3409; A61B 2017/003; A61B 2017/00292; A61B 2017/00296; A61B 2010/045; A61B 10/04; A61M 25/0116; A61M 25/0113; A61M 2025/0166
  See application file for complete search history.

(56) References Cited

U.S. PATENT DOCUMENTS

| | | |
|---|---|---|
| 2004/0097805 A1 | 5/2004 | Verard et al. |
| 2008/0287963 A1 | 11/2008 | Rogers et al. |
| 2009/0012533 A1 | 1/2009 | Barbagli et al. |
| 2010/0280449 A1 | 11/2010 | Alvarez et al. |
| 2010/0331820 A1 | 12/2010 | Prisco et al. |
| 2011/0065993 A1 | 3/2011 | Belson et al. |
| 2011/0202069 A1 | 8/2011 | Prisco et al. |
| 2011/0319714 A1 | 12/2011 | Roelle et al. |
| 2013/0109957 A1 | 5/2013 | T'Hooft et al. |
| 2013/0204124 A1 | 8/2013 | Duindam et al. |
| 2014/0171919 A1 | 6/2014 | Blacker |
| 2015/0351608 A1 | 12/2015 | Choi |
| 2017/0281287 A1 | 10/2017 | Au |
| 2017/0281288 A1 | 10/2017 | Au |

FOREIGN PATENT DOCUMENTS

| | | |
|---|---|---|
| WO | WO-2011046028 A1 | 4/2011 |
| WO | WO-2011100124 A1 | 8/2011 |
| WO | WO-2013056006 A2 | 4/2013 |

OTHER PUBLICATIONS

Extended European Search Report for Application No. EP15840939.1, mailed on May 4, 2018, 5 pages.
Extended European Search Report for Application No. EP18204688.8, mailed on Feb. 21, 2019, 8 pages.
International Preliminary Report on Patentability for Application No. PCT/US2015/048254, mailed on Mar. 23, 2017, 7 pages.
International Search Report and Written Opinion for Application No. PCT/US2015/048254, mailed on Dec. 17, 2015, 13 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

SYSTEM WITH GUIDES AND TOOLS OF DIFFERENT FLEXIBILITY

RELATED APPLICATIONS

This application is a continuation of U.S. patent application Ser. No. 15/509,062, filed Mar. 6, 2017 (now issued as U.S. Pat. No. 10,939,972), which is the U.S. national phase of International Patent Application No. PCT/US2015/048254, filed Sep. 3, 2015; which designated the U.S. and claims priority to and the benefit of U.S. Provisional Application No. 62/048,210, filed Sep. 9, 2014, all of which are incorporated by reference herein in their entireties.

BACKGROUND

Many types of minimally invasive medical procedures involve inserting a guide tube to a target site and then inserting and removing one or more tools through the guide tube. In some procedures, the guide tube may be flexible enough to follow a natural lumen, but the tool or a portion of the tool may not be as flexible as the guide tube. As a result, insertion or removal of the tool may be difficult. For example, a biopsy needle at the distal end of a lung biopsy instrument may be stiffer than the lung catheter used to guide the lung biopsy instrument. During a lung biopsy, a lung catheter following branching airways may bend to an extreme angle in order to reach a targeted nodule, and the biopsy needle may be difficult to push or insert through the sharp bend in the catheter. In particular, when a biopsy needle is being inserted through a catheter, a physician may apply an insertion force intended to slide the needle along a tool lumen in the catheter, and the walls of the tool lumen may apply a force that deflects or even bends the biopsy needle as the needle is being inserted. However, the interaction of the needle with the walls of the tool lumen causes friction and may cause the needle to dig into the catheter, making insertion of the tool difficult. Also, an insertion force that is too large may damage the biopsy needle or the catheter. Similarly, when removing a tool from a convoluted guide tube, the stiff part of the tool may be difficult to pull through sharp bends without applying potentially damaging force. Systems and methods for efficient insertion and removal of tools from flexible guide tubes are thus desired.

SUMMARY

In accordance with an aspect of the invention, a robotically controlled medical system can determine and record the shape of a guide tube in a target configuration. If the shape of the flexible guide tube in the target configuration includes one or more bend with a radius of curvature that is sharper than the predetermined minimum radius of curvature or if the target configuration is otherwise unsuitable for insertion/removal of a tool, a control system for the tool can inform a user to activate or can automatically activate a tool insertion/removal mode. In the tool insertion/removal mode, the control system identifies a configuration of the guide tube suitable for insertion or removal of the tool. This insertion/removal configuration may, for example, be a configuration in which the distal end of the guide tube is pulled back to a location that is along the target configuration and associated with the most proximal bend having a radius of curvature less than a minimum permitted radius. The control system when in the tool insertion/removal mode can automatically retract distal tip of the guide tube substantially along the recorded shape until the guide tube is in the insertion/removal configuration. The tool can then be inserted or removed without requiring excessive or damaging force. The control system can then automatically return the guide tube, e.g., containing the inserted tool, along the recorded shape back to the target configuration. For return of the guide tube from the insertion/removal configuration to the target configuration, a stiffer part of the tool, e.g., the needle in a biopsy instrument, may be within the steerable section of the guide tube, so that the steerable section may bend or flex the tool as needed to automatically retrace the recorded shape and return the guide tube to the target configuration. Removal of the tool can be the reverse of the insertion process. In particular, the guide tube containing the tool may be retracted from the target configuration to the insertion/removal configuration where the tool can be removed without need of excessive force. A tool can thus be inserted before use and removed or replaced after use without damaging the tool or guide tube, without requiring large insertion/removal force, and without requiring medical personnel to manually navigate the guide tube repeatedly between the target configuration and an insertion/removal configuration.

One specific embodiment is a medical system including a guide tube with a steerable distal tip, a drive system, and control logic. The drive system may control pitch and yaw of the distal tip of the guide tube, control the shape of the distal portion of the guide tube, and/or control movement of the guide tube along an insertion direction. The control logic operates the drive system and may include a shape analysis module and a movement module. For example, the shape analysis module may identify bends in a target configuration of the guide tube that are too sharp for a tool to easily traverse, and the movement module may control the drive system for automatic movement of the guide tube between the target configuration and an insertion/removal configuration, which may correspond to the distal tip of the guide tube being at a location associated with a bend that is too sharp for the tool to traverse.

DETAILED DESCRIPTION

Many minimally invasive medical procedures involve inserting a guide tube to a target site and then inserting and removing one or more tools through the guide tube. In some of these procedures, the guide tube is flexible enough to follow a natural lumen and position a distal tip of the guide tube at a target location with a target orientation. The guide tube after being steered to its target location has what is referred to herein as a target configuration, and in the target configuration, the guide tube may have a shape conforming to the shape of the natural lumen with no or minimal distortions. Steering the guide tube to the target configuration is typically a process that may require a physician's time and attention. For example, a physician may use a control device, e.g., a joystick, to control a steerable portion of the guide tube and may select a path for insertion of the guide tube based on video images from the perspective of the distal tip of the guide tube or from the perspective of an external imaging or sensing device. Once the guide tube is in the target configuration, the physician may try to insert a tool through the guide tube until the distal tip of the tool extends from the distal end of the guide tube, where the tool may be used in a medical procedure such as collecting body tissue samples. However, the shape of the guide tube in the target configuration may be such that insertion of the tool is difficult or impossible without inconvenience or even risking damage to the tool, the guide tube, or a patient.

Figure 1:
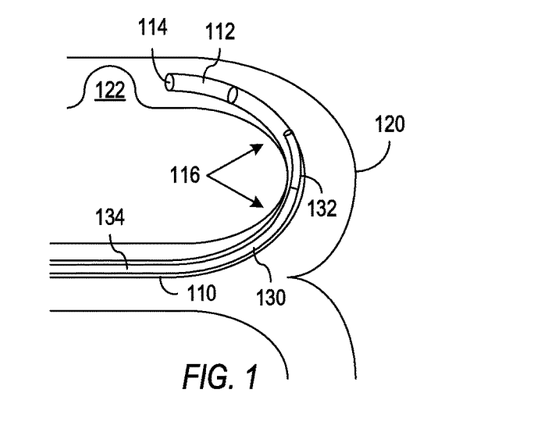
FIG. 1 illustrates a failed attempted to deploy a biopsy needle through a lung catheter having a sharp bend.

FIG. 1 illustrates a situation in which the guide tube is a lung catheter 110 that is deployed through airways 120 to a target configuration in which a distal tip of catheter 110 points at a nodule 122. Catheter 110 may be a flexible guide tube having at least one tool lumen for guiding of a tool such as a biopsy needle 130 or other medical probe. Catheter 110 may particularly be a steerable device, e.g., having an actuated distal section 112 capable of controlling the pitch and yaw of a distal tip 114 of catheter 110. Distal section 112 may, for example, be controlled by pulling on cables or tendons (not shown) that extend from distal section 112 along the length of catheter 110 to a drive mechanism (not shown). Catheter 110 may also be steerable using a computerized control system that operates the drive system to control the pitch and yaw of tip 114, the shape of distal section 112, or the length of catheter 110 inserted through airways 120.

A user such as a physician may deploy lung catheter 110 by first introducing tip 114 to the bronchial system of a patient. In one implementation, a biopsy instrument 130 is not in catheter 110 during initial deployment of catheter 110. For example, a removable camera system (not shown) may be inserted in the main or tool lumen of catheter 110 during the initial deployment of catheter 110. Alternatively, catheter 110 may include a permanent vision system (not shown) that leaves the main lumen available for a tool such as biopsy needle 130. In either case, a user such as a physician can view the bronchial system through a vision system that provides the perspective of tip 114 or can use an external sensor system to identify the location of distal tip 114 relative to airways 120. The user can then manipulate a master controller such as a joystick to control the pitch and yaw of distal tip 114 and movement of catheter 110 along an insertion axis, and in that way, navigate distal tip 114 to a target configuration for a biopsy of a nodule 122 in airways 120. During the navigation, a computer system can mediate pitch, yaw, and insertion movement of distal tip 114, or some or all of the movement of catheter 110 may be under direct manual or tactile control. Sec, for example, co-filed U.S. patent application Ser. No. 15/509,154, entitled "Flexible Medical Instrument," which is hereby incorporated by reference in its entirety. FIG. 1 illustrates catheter 110 after reaching a target configuration, regardless of the technique used to reach the target configuration.

Biopsy needle 130 generally includes a needle section 132 that may be made of a material such as stainless steel attached to the distal end of a more compliant section 134 made from a material such as Polytetrafluoroethylene. In general, section 132 may be stiffer, less flexible, or less compliant than catheter 110 or section 134, and section 134 may be at least as flexible or compliant as catheter 110. The target configuration of catheter 110 may include many bends, and in FIG. 1, catheter 110 has a bend 116 with a radius of curvature and an angular size such that a tip or needle section 132 of a biopsy needle 130 is unable to traverse bend 116 without application of an insertion force that is unacceptably large. As a result, needle section 132 may wedge against the interior walls of the tool lumen in catheter 110. A more flexible needle section 132 could be employed to allow needle section 132 to more easily traverse sharp bends such as bend 116, but making needle section 132 more flexible or floppy may make taking a biopsy sample more difficult. In general, tools require stiffness in order to perform their intended medical task, so that configurations of guide tube 110 in which a tool 130 such as biopsy needle 130 cannot be fully advanced to the distal tip of guide tube 110 may occur.

A physician manually inserting biopsy needle 130 through catheter 110 may feel resistance to insertion of needle 130 greatly increase when needle 130 reaches bend 116 and may then know that needle 130 cannot be fully deployed through catheter 110 while catheter 110 is in the target configuration. Similarly, if a physician navigates a guide tube such catheter 110 containing a tool such as biopsy needle 130 to a target configuration containing a sharp bend, the physician may find that a sharp bend 116 halts removal of the tool. In one implementation, a physician may encounter a situation in which a tool such as biopsy needle 130 cannot be further advanced or retracted through a guide tube such as catheter 110 without unacceptable force or risk and may activate an insertion/removal control mode that performs automated movements of the guide tube as described further below. For example, a control system for catheter 110 may automatically, partially retract catheter 110 to a tool insertion configuration in which needle 130 can be inserted before catheter 110 with the inserted tool 130 is automatically returned to the target configuration. Similarly, the control system for catheter 110 may automatically retract catheter 110 containing biopsy needle 130 to a tool removal configuration where needle 130 can be removed and catheter 110 can remain ready for insertion of a replacement tool. In general, the insertion configuration may be the same as or different from the removal configuration, and the insertion/removal configuration is used herein to refer to a configuration that an insertion configuration or a removal configuration.

As an alternative to having a human user identify a problem with insertion or removal of a tool, a control system for a guide tube such as a lung catheter can measure and evaluate the shape of the guide tube in its target configuration to determine whether a tool can be inserted or removed along the target configuration of the guide tube without requiring unacceptable force or unacceptable risk. If the target configuration is unsuited to insertion or removal of the tool, the control system can inform a physician and determine a tool insertion/removal configuration suitable for insertion or removal of the tool. The physician can then choose to use the insertion/removal control mode, or the control system can automatically switch to the insertion/removal control mode without need of human intervention.

Figure 2:
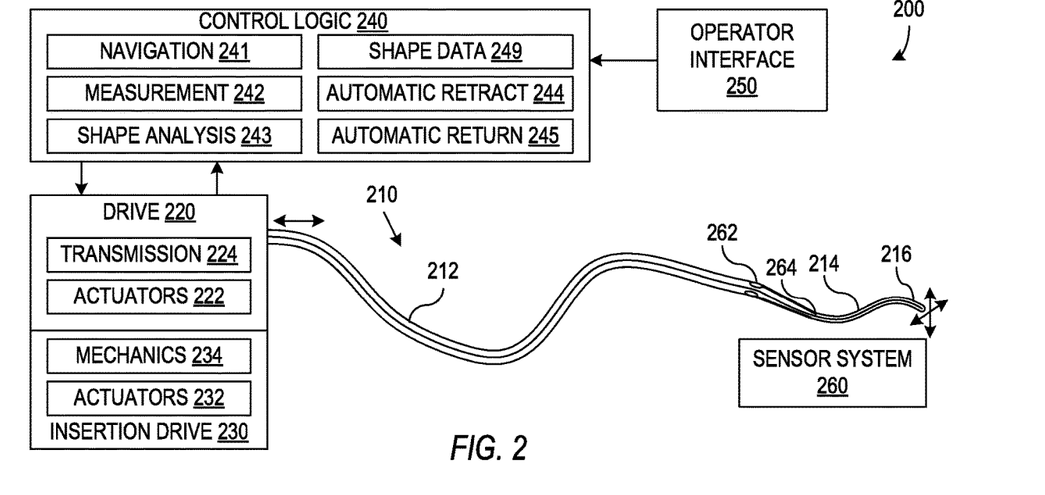
FIG. 2 is a block diagram of one implementation of a medical system including a lung catheter.

FIG. 2 schematically illustrates one specific implementation of a medical system 200 in accordance with one embodiment of the invention. In the illustrated embodiment, system 200 includes a lung catheter 210, a steering drive mechanism 220, an insertion drive mechanism 230, control logic 240, an operator interface 250, and a sensor system 260.

Figure 3A:
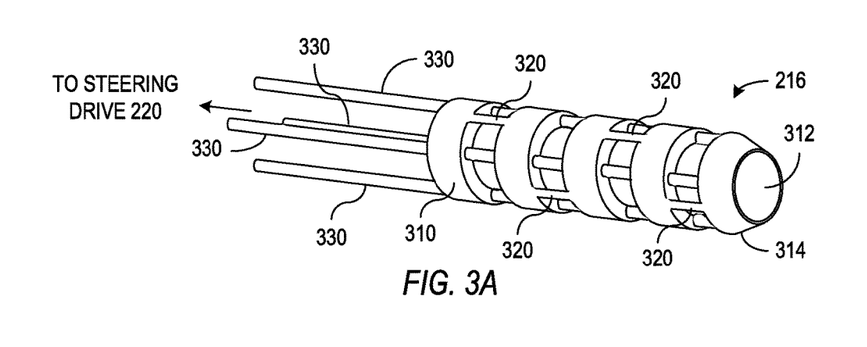
FIGS. 3A and 3B show alternative implementations of a distal tip of a flexible instrument.
Figure 3B:
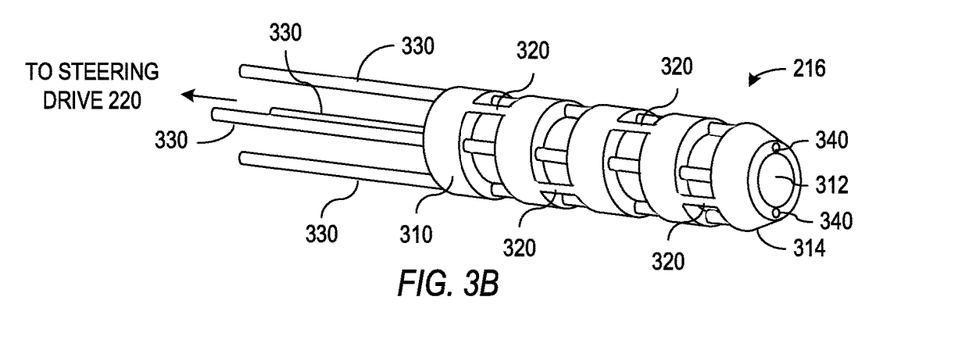

Catheter 210 is a generally flexible device having one or more lumens including a tool lumen that can accommodate interchangeable probes such as a biopsy need or a vision system. Flexible catheters can be made using a braided structure such as a woven wire tube with inner or outer layers of a flexible or low friction material such as polytetrafluoroethylene (PTFE). In one embodiment, catheter 210 includes a bundle of lumens or tubes held together by a braided jacket and a reflowed (i.e., fused by melting) jacket of a material such as Polyether Block Amide (Pebax). A stecrable distal section 216 (e.g., a structure such as shown in FIG. 3A or 3B and described further below) can form part of the distal end of catheter 210.

Catheter 210 as noted above includes at least one tool lumen for interchangeable probe systems and may further include smaller lumens for pull wires, sensor lines, illumination fibers, or permanent vision systems or for introduction or removal of fluids or medication to or from a work site. In the illustrated embodiment, catheter 210 has a proximal section 212 attached to steering drive mechanism 220 and a distal section 214 that extends from proximal section 212. In the illustrated implementation, distal section 214 includes steerable section 216, which has a mechanical structure that may be actuated through pull wires that extend from steering drive mechanism 220 through proximal section 212 and distal section 214 and connect to steerable distal segment 216. Alternatively or additionally, mechanical elements anywhere along the length of catheter 210 may be similarly articulated or actuated using drive tendons or other mechanisms.

The overall length of catheter 210 for procedures performed in lungs or airways may be about 60 to 80 cm or longer with distal section 214 being about 15 cm long and steerable segment 216 being about 4 to 5 cm long. Distal section 214 may have a smaller diameter than does proximal section 212. During a medical procedure, a portion of proximal section 212 and all of distal section 214 may be inserted along a natural lumen such as an airway of a patient. A smaller diameter for distal section 214 may permit use of distal section 214 in lumens that are too small for proximal section 212, but a larger diameter for proximal section 212 may facilitate manual manipulation or inclusion in proximal section 212 of more or larger structures or devices such as electromagnetic sensing coils 262 that may not fit in distal section 214.

Steerable segment 216 is remotely controllable and particularly has a pitch and a yaw that can be controlled using actuating tendons, e.g., pull wires. Stecrable segment 216 may form all or part of distal section 214 and may be simply implemented as a multi-lumen tube of flexible material such as Pebax with suitable connections to the actuating tendons. Steerable segment 216 may be more flexible than the remainder of catheter 210 to assist in isolating actuation or bending to steerable segment 216 when steering drive mechanism 220 pulls on actuating tendons. Catheter 210 can also employ additional features or structures such as use of Bowden cables for actuating tendons to prevent actuation from bending proximal section 212 (or bending any portion of distal section 214 other than steerable segment 216). However, the entirety of catheter 210 should have sufficient compliance and a sufficiently small minimum radius of curvature to follow or conform to the shape of a natural lumen, e.g., airways.

FIG. 3A shows one specific embodiment in which steerable segment 216 is made from a tube 310 that in catheter 210 of FIG. 2 defines the distal end of a main lumen 312 for a probe system and contains smaller lumens for actuating tendons 330 and for a shape sensor not shown in FIG. 3A. In particular, main lumen 312, which continues back through catheter 210, has an opening at the distal tip 314 of steerable segment 216, and a tool such as a biopsy needle inserted through main lumen 312 can extend past distal tip 314 to interact with tissue during a medical procedure. In the illustrated embodiment, four tendons 330 are placed 90° apart and surrounding lumen 312 to facilitate steering instrument 110 in pitch and yaw directions defined by the locations of tendons 330. A reflowed jacket, which is not shown in FIG. 3A to better illustrate the internal structure of steerable segment 316, may also cover tube 310. As shown in FIG. 3A, tube 310 is cut or formed to create a series of flexures 320. Tendons 330 connect to distal tip 314 of steerable segment 216 and extend back to steering drive mechanism 220. Tendons 330 can be wires, cables, Bowden cables, hypotubes, or any other structures that are able to transfer force from steering drive mechanism 220 to distal tip 314 and capable of limiting the bending of proximal section 212 when steering drive mechanism 220 pulls on tendons 330. In operation, pulling harder on any one of tendons 330 tends to cause stecrable segment 216 to bend in the direction of that tendon 330. To accommodate repeated bending, tube 310 may be made of a material such as Nitinol, which is a metal alloy that can be repeatedly bent with little or no damage.

The implementation of steerable section 216 shown in FIG. 3A does not include a camera or other elements of a vision system that can provide a user with a view, e.g., a stereoscopic view, from the perspective of distal tip 314. However, a probe that includes a vision system can be inserted through main lumen 312 to provide a view to a user, for example, during navigation of catheter 210 along a natural lumen such as an airway. A vision probe may be removed for replacement with another tool or probe such as a biopsy needle. Alternatively, as shown in FIG. 3B, a steerable section 216 may include permanent components 340 of a vision system, so that a probe such as a biopsy needle may reside in main lumen 312 while the vision components 340 are in operation. Vision components 340 may include, for example, a camera system, an illumination system, or the ends of optical fibers that carry illumination or image light between the distal and proximal ends of catheter 210.

Steering drive mechanism 220 of FIG. 2, which pulls on tendons 330 to actuate distal steerable segment 216, includes a mechanical system or transmission 224 that converts the movement of actuators 222, e.g., electric motors, into movements of or tensions in tendons 330 that run through catheter 210 and connect to distal steerable segment 216. The movement and pose of distal steerable segment 216 can thus be controlled through computerized selection or generation of respective actuation signals for actuators 222 in steering drive mechanism 220. In addition to actuation of steerable segment 216, steering drive mechanism 220 may be used to control other movement of catheter 210 such as rotation or roll of the proximal end of catheter 210, which may also be powered through actuators 222 and transmission 224. Backend mechanisms or transmissions that are known for flexible-shaft instruments could in general be used or modified for steering drive mechanism 220. For example, some known drive systems for flexible instruments are described in U.S. Pat. App. Pub. No. 2010/0331820, entitled "Compliant Surgical Device," which is hereby incorporated by reference in its entirety. Steering drive mechanism 220 in addition to actuating catheter 210 should allow removal and replacement of probes in catheter 210, so that the structure of drive mechanism 220 should be out of the way during such operations.

In the illustrated implementation of FIG. 2, steering drive mechanism 220 is mounted on insertion drive mechanism 230, which includes actuators 232 and a mechanical system 234 used to move steering drive mechanism 220 and catheter 210 along the insertion direction. Mechanical system 234 may include a slide or a track on which steering drive mechanics 220 is movably mounted. Actuators 232 may be drive motors that power movement of steering drive mechanics 220 and catheter 210 according to actuation signals that control logic 240 selects or generates.

Control logic 240 controls actuators 222 in steering drive mechanism 220 to selectively pull on the tendons as needed to actuate distal steerable segment 216 and control the pitch and yaw of the distal tip of catheter 210 and controls actuators 232 to control movement in the insertion direction of the distal tip of catheter 210. In general, control logic 240 operates in response to commands from a user, e.g., a surgeon, physician, or other human user using operator interface 250, and the user may operate interface 250 in response to a view that a vision system provides or measurements from sensor system 260. Control logic 240 may be implemented using a general purpose computer with suitable software, firmware, and/or device-specific interface hardware to interpret signals from operator interface 250 and sensor system 260 and to generate actuation signals for actuators 222 and 232.

In the illustrated embodiment, control logic 240 includes multiple modules 241, 242, 243, 244, and 245 that implement different processes or modes for use of catheter 210. As used herein, the term "module" refers to a combination of hardware (e.g., a processor such as an integrated circuit or other circuitry) and software (e.g., machine- or processor-executable instructions, commands, or code such as firmware, programming, or object code). A combination of hardware and software includes hardware only (i.e., a hardware element with no software elements), software hosted at hardware (e.g., software that is stored at a memory and executed or interpreted or at a processor), or hardware and software hosted at hardware.

Navigation module 241 may be employed while a user steers catheter 210 to a target location or configuration. Navigation module 241 may act to interpret or convert control signals from operator interface 250 and to generate actuation signals for actuators 222 and 232. Operator interface 250 may include standard input/output hardware such as a vision system, a display, a keyboard, a joystick, a foot pedal, a pointing device such as a mouse, or similar I/O hardware that may be customized or optimized for a surgical environment. In general, operator interface 250 provides information to the user and receives instructions from the user. For example, operator interface 250 may indicate the status of system 200 and provide the user with data including images and measurements made in system 200. One type of instruction that the user may provide through operator interface 250, e.g., using a joystick or similar master controller, indicates the desired pitch, yaw, and insertion movement of distal steerable segment 216. Using such inputs, control logic 240 can generate actuation signals for actuators 222 and 232 in drive mechanisms 220 and 230. Other instructions from the user may select an operating mode of control logic 240.

Shape measurement module 242 may be employed to measure or record the shape of catheter 210, for example, during or after navigation of catheter 210 to a target configuration for a medical procedure. For example, after a user has employed navigation module 241 and used operator interface 250 to navigate catheter 210 to a target configuration, shape measurement module 242 may be employed to determine and record shape data 249 indicating the shape of at least a distal portion of catheter 210. In the implementation of FIG. 2, a fiber optic shape sensor 264 may extend along the entire length or a distal portion of catheter 210, so that shape measurement module 242 can use measurements of the interference of light transmitted on optical fiber, determine the shape of at least a portion of catheter 210, and store shape data 249 in memory or other storage that control logic 240 employs. Such shape sensors using fiber gratings are further described in U.S. Pat. No. 7,720,322, entitled "Fiber Optic Shape Sensor," which is hereby incorporated by reference in its entirety. Other implementations could use other systems for sensing the shape of a distal portion of catheter 210. In one implementation, distal steerable section 216 has the greatest ability to bend, and bends that are too sharp for insertion of a tool may be exclusively or most common at or near distal steerable section 216 when catheter 210 is in the target configuration.

Shape analysis module 243 can be used to analyze shape data 249, particularly for operations such as insertion or removal of a tool in catheter 210. For example, when a user desires to insert a tool such as a biopsy needle along the deployed shape of catheter 210, shape analysis module 243 can use shape data 249 and possibly data regarding the tool to identify any bend in catheter 210 that is too sharp for the tool to traverse. More generally, shape analysis module 243 can determine whether a specific tool can be deployed through or removed from catheter 210 while catheter 210 has a target configuration and identify an insertion or removal configuration of catheter 210 generally or for that specific tool. Automatic retract module 244 can then be employed to automatically (i.e., without user steering) move the distal tip 216 of catheter 210 back along the shape indicated by shape data 249 from the target configuration to the insertion or removal configuration of catheter 210. For example, retract module 244 may automatically retract catheter 210 just far enough that a specific tool can be inserted to the distal tip of catheter 210 without undue force or risk. Return module 245 may then automatically return catheter 210 to the target configuration by steering the distal tip along the path that shape data 249 indicates. Although separate modules are shown in FIG. 2, the functions of multiple modules may be combined into a single module, e.g., an automatic retract/return module.

Figure 4:
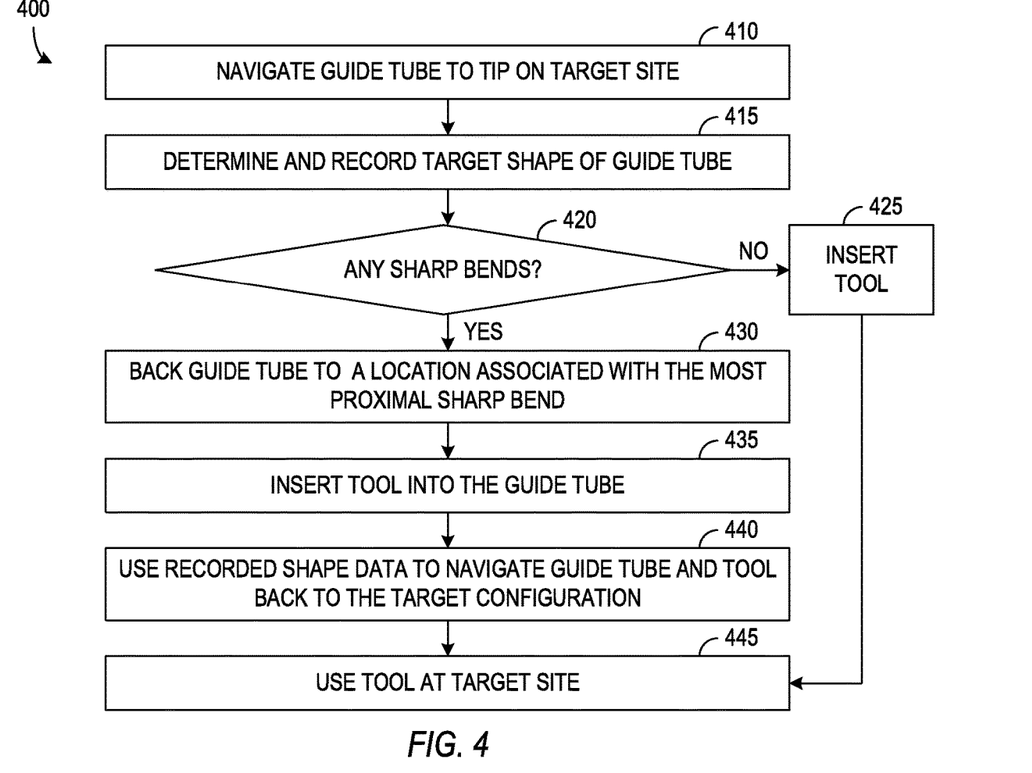
FIG. 4 is a flow diagram of an example process for deploying a tool through a flexible guide tube.
Figure 5A:
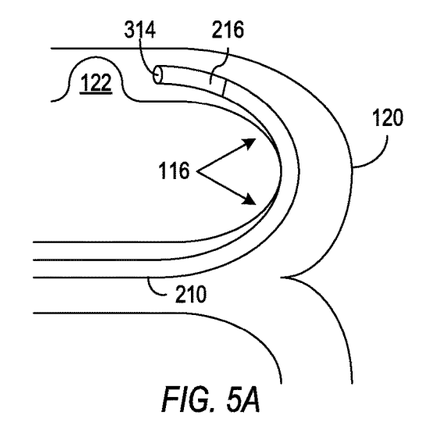
FIG. 5A shows an empty guide tube deployed to a target configuration.

FIG. 4 is a flow diagram of a process 400 for use of a guide tube with a tool that may be unable or not permitted to traverse the guide tube in the target configuration. To provide a definite example, process 400 is sometimes described herein with reference to the structure of FIG. 2 and the illustrated configurations of FIGS. 5A to 5E, but more generally, process 400 is not limited to specific hardware illustrated in FIG. 2 or the specific configurations of FIGS. 5A to 5E. Process 400 begins with a block 410 in which the guide tube, e.g., catheter 210, is steered to a target configuration as shown in FIG. 5A. For example, a user may activate a navigation mode implemented with navigation module 241 of system 200 and then control user interface 250 as needed to direct catheter 210 through airways of a patient. Such navigation might include selecting branches of airways to follow and controlling the pitch and yaw of distal section 216 of catheter 210 to follow selected airways to nodule 122. The guide tube may be empty during performance of navigation block 410 or may include a probe such as a vision system if the guide tube does not possess a permanent vision system.

In one implementation of process 400, a physician, after navigation to the target configuration but before inserting a tool in the guide tube, presses a button or otherwise activates an insertion/removal mode of the medical system associated with a guide tube. A block 415 of process 400 determines and records shape data indicating the shape of the guide tube in the target configuration. Many techniques for measuring the shape of the guide tube can be used. For example, catheter 210 includes a fiber optic grating sensor 264 that may be used as described in U.S. Pat. App. Pub. No. 2009/0324161, entitled "Fiber Optic Shape Sensor," which is hereby incorporated by reference in its entirety. With a fiber optic grating sensor, the shape of all or a distal portion of catheter 210 in the target configuration of FIG. 5A can be measured. Alternatively, the shape of catheter 210 may be determined by tracking the navigation or movement of the distal tip of instrument 210 to its target configuration during process 410. The measured or otherwise determined shape of catheter 210 can be recorded, e.g., stored in memory or other storage in control system 240 for catheter 210. For example, the determined shape may be recorded as shape data 249 in any desired format.

The shape data can be analyzed in decision block 420 to identify any locations in or sections of the target configuration through which insertion of a tool is contraindicated. For example, shape analysis module 243 may identify the locations of any bends in the target configuration of the guide tube that are too sharp for a desired tool to traverse without application of an insertion force deemed to be too large. A sharp bend, for example, may be a section of catheter 210 that extends for more than a specific distance or angle and has a radius of curvature that is less than the minimum permitted bend radius. For example, shape analysis module 243 may determine a radius of curvature at each of a series of points associated with the shape data and compare each determined radius of curvature to a minimum permitted radius of curvature for the specific tool. The minimum permitted bend radius may be selected according to the tool being inserted and may depend on, for example, the coefficient of friction between the tool and guide tube, the stiffness and length of a critical section of the tool, the stiffness of the guide tube, the stiffness tissue supporting the guide tube, and other factors. Alternatively, an "empirical table" may be developed that indicates whether a section of guide tube is problematic and may be indexed by factors such as flexibility of the tool or the smallest radius of curvature the tool can accommodate without damage, the radius of curvature of a section of the guide tube, the stiffness of the guide tube, and the stiffness of tissue surrounding the section of the guide tube. More generally, shape analysis module 243 could use any desired criterion to evaluate each section of the shape data and determine or identify problem sections. In general, a section is a problem if pushing or pulling the tool through the section requires an unacceptable level of force, and an unacceptable level of insertion force may be selected based on, for example, risk to a patient, risk of damage to the guide tube or tool, or convenience of use of the tool. FIGS. 5A to 5E illustrate a situation in which only a single section, bend 116, is a problem for insertion of a tool through the guide tube. More generally, zero, one, or multiple problem sections may be found. Shape analysis module 243 can determine an insertion or removal configuration of the guide tube as being the longest proximal portion of the target configuration that does not include any problem sections.

Figure 5B:
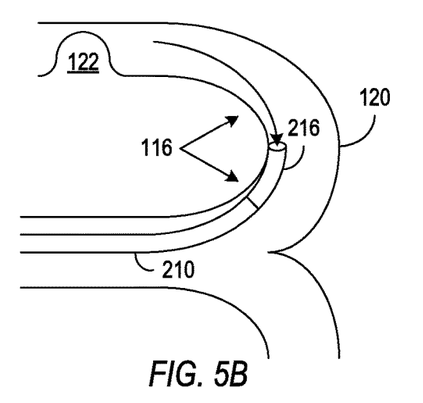
FIG. 5B illustrates the retraction of the empty guide tube from the target configuration of FIG. 5A to an insertion or removal configuration.
Figure 5C:
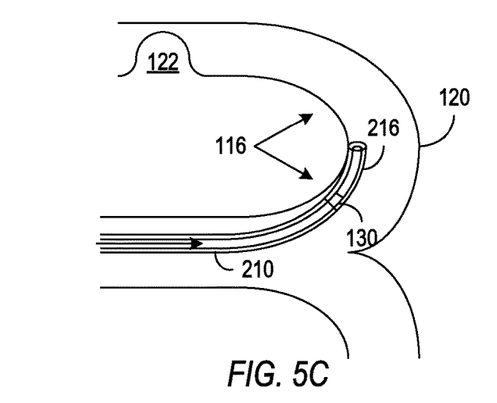
FIG. 5C illustrates the guide tube in an insertion or removal configuration of FIG. 5B after a tool has been inserted.
Figure 5D:
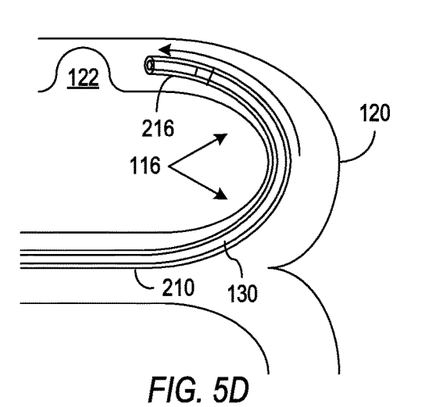
FIG. 5D illustrates navigation of the guide tube containing the tool between the insertion or removal configuration of FIG. 5C and the target configuration of FIG. 5A.
Figure 5E:
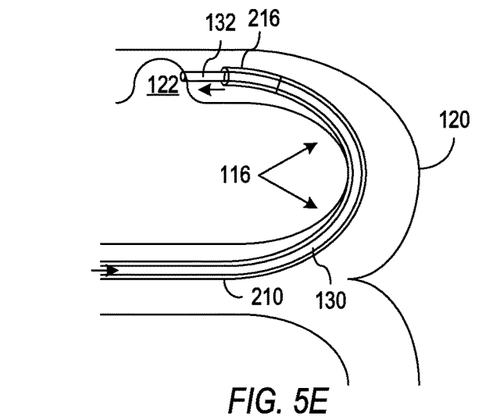
FIG. 5E illustrates a tool being inserted further for use in a medical procedure after the guide tube was returned to the target configuration.

If a decision block 420 determines that the entire target configuration is acceptable for insertion of the tool, a block 425 can be performed during which the tool is inserted to the distal tip of the guide tube while the guide tube remains in the target configuration as shown in FIG. 5D and the tool may be used as described below with reference to FIG. 5E.

If decision block 420 determines that the target configuration of the guide tube is unacceptable for insertion of the tool, e.g., the target configuration includes bends that are too sharp for insertion of the tool, a physician or other user may be informed and may press a button or otherwise select to retract the guide tube to the identified insertion configuration. In FIG. 4, a block 430 retracts the distal tip of the guide tube back to a location associated with an acceptable configuration, e.g., a location just before the most proximal problem section of the guide tube in the target configuration or the most proximal bend that is too sharp for the tool as shown in FIG. 5B. Block 430 thus moves guide tube from the target configuration of FIG. 5A to an insertion or removal configuration as shown in FIG. 5B. In general, the guide tube is only partially retracted, i.e., not fully removed, for example, because the sharpest bends in the guide tube may be expected to be close to the distal end of the target configuration. Retraction of the guide tube in block 430 can be performed automatically, i.e., without the need of a user to steer the guide tube. For example, in system 200 of FIG. 2, a user or control logic 240 on its own initiative may engage retract module 244, which automatically generates actuation signals for actuators 222 and 232 from shape data 249, without using or needing control signals from operator interface 240.

The user can then manually insert the tool into the guide tube. In block 435, the tool is inserted to the distal tip of the guide tube while the guide tube remains in the insertion configuration such as shown in FIG. 5C. More generally, the tip of biopsy needle 130 may be inserted past distal tip 114 or may be short of distal tip 114. Whether a needle is best inserted to the distal tip of the guide tube, past the distal tip of the guide tube, or short of the distal tip of the guide may depend on factors such as the stiffness or minimum radius of curvature of the critical section of the tool and the amount of actuation force that the steerable section of the guide tube can apply to the critical section of the tool. For example, when a tool such as a biopsy needle is soft enough that it is bendable by the actuated pitch and yaw of the guide tube, the needle can be inserted to the tip of the catheter, and the catheter-needle union can just proceed to the target configuration along the recorded path either automatically or manually. If the needle is very stiff, the system can recommend to the user how much the needle needs to be inserted past (or short of) the distal tip of the catheter to maintain a reasonable catheter-needle stiffness so that the catheter-needle union can still proceed forward with the recorded path. If the catheter-needle union is too stiff to follow the previously recorded path, the user may still drive the catheter manually. As noted above, retracting to an insertion configuration allows the tool to be inserted, and at that point, an approach for returning to the target configuration can be chosen.

Performance of block 440, in many situations, can automatically return the guide tube with the tool inserted back to the target configuration indicated by the recorded shape data as illustrated in FIG. 5D. Catheter 210 can take tool 130 through the problem section or tight bend 116 since actuation of steerable distal section 216 may be generally better able to bend the stiffer section 132 of tool 130 when compared to the force from the walls of catheter 210 resulting from insertion force applied to the proximal end of tool 130. Once the guide tube with the tool reaches the target configuration, block 445 can be performed to use the tool at the target site. For example, a tool such as a biopsy needle can be extended beyond the distal tip of the guide tube to interact with (e.g., sample) tissue as shown in FIG. 5E.

Figure 6:
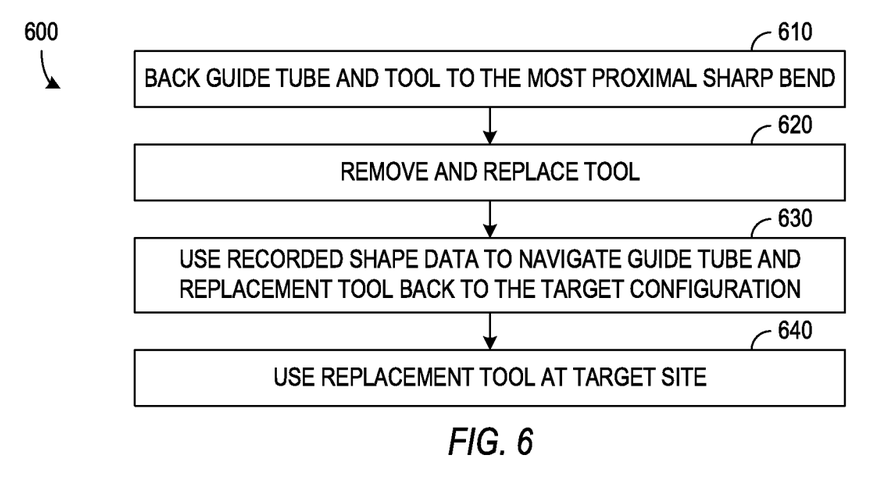
FIG. 6 is a flow diagram of an example process for removing a tool from a flexible guide tube.

Sharp bends or problem sections in a guide tube can also be an issue when removing a tool having at least a portion that is less flexible than the guide tube. FIG. 6 is a flow diagram of a process 600 for removal of a tool from a guide tube that is deployed to a target configuration including a bend that is too sharp for the tool to traverse without bending to a radius of curvature smaller than the minimum radius of curvature permitted for the tool. Process 600 begins with performance of a block 610 that backs the guide tube and tool back to a location just before the most proximal problem section, e.g., a location associated with the most proximal bend that is too sharp. Once at that location, performance of block 620 may remove and replace the tool while the distal tip of the guide tube remains in the insertion/removal configuration. Assuming that the replacement tool has a minimum permitted radius of curvature that is the same as or smaller than the radius of curvature of the removed tool, performance of block 620 may leave the guide tube in the same position. For example, a biopsy needle that has taken a tissue sample can be replaced with a new biopsy needle of the same type, which may be used to take a second tissue sample at the target site. Step 630 can then use the recorded shape data to automatically navigate the guide tube and the inserted replacement tool back to the target configuration of the guide tube. Performance of block 640 can then use the replacement tool at the target site.

The automatic retract and return as disclosed above may have advantages over similar manual procedures. In particular, a physician deploying the biopsy needle through a catheter could manually retract the catheter to some location at which the biopsy needle can be inserted to the end of the catheter. In general, the manual retraction will take longer than an automated process and generally will retract the guide tube more than is strictly necessary. The physician may then also need to manually navigate the catheter with the biopsy needle back to the target location and configuration. The manual back and forth procedure can be very time consuming and creates opportunities for errors because the physician often needs to do multiple biopsies for the same site, which requires the physician to navigate the catheter multiple times through the same airway or airways. The automatic retract and return processes may take less time than physician controlled movements. Further, these procedures if controlled by the physician may require a vision system for the physician and therefore would be difficult or impossible to perform with a catheter lacking a permanent vision system. Catheters with permanent vision systems may be expected to either be larger or have a smaller main lumen in order to allow space for a vision system, so that the automatic retraction and return may allow use of smaller catheters that fit within smaller airways. Further, even if the catheter has a vision system, if a nodule to be biopsied is located in the area in which the camera or other vision system is ineffective such as in a mucus airway or if the nodule is located in a small lumen into which the catheter does not fit, the physician controlled back-and-forth motion may not guarantee that the catheter and biopsy needle returns to the targeted location and configuration.

Some implementations described above may efficiently provide a robust, reliable, repeatable, precision biopsy process that requires only permitted amounts of insertion force or bending at the tip of the biopsy needle even when a catheter or other guide tube for the biopsy needle includes sharp bends. Automated navigation for retraction and return during a biopsy procedure can be based on recorded shape data and may save a tremendous amount of time, particularly when multiple samples need to be taken from the same nodule. The work force required in a biopsy procedure may also be reduced when compared to a biopsy task that may take more than one physician. For example, in conventional procedures, one physician may be charged with navigating the bronchoscope while the other controls the deployment of the needle. With the systems and procedures described herein, a single physician may be sufficient because the amount of force required to insert a biopsy needle may be reduced. The automation of repeated backing and return along the same airways may also be able to reduce human errors created during such biopsies.

Some embodiments of the above invention can be implemented in a computer-readable media, e.g., a non-transient media, such as an optical or magnetic disk, a memory card, or other solid state storage containing instructions that a computing device can execute to perform specific processes that are described herein. Such media may further be or be contained in a server or other device connected to a network such as the Internet that provides for the downloading of data and executable instructions.

Although particular implementations have been disclosed, these implementations are only examples and should not be taken as limitations. Various adaptations and combinations of features of the implementations disclosed are within the scope of the following claims.

What is claimed is:
1. A system comprising:
an actuator couplable to a flexible guide tube and configured to move at least a portion of the flexible guide tube;
a processor; and
memory storing computer-executable instructions that, when executed by the processor, cause the system to:
identify at least one factor associated with insertion or removal of a tool configured to be inserted through or removed from the flexible guide tube;
identify, in a first configuration of the flexible guide tube and based on the at least one factor, one or more sections of the flexible guide tube having one or more bends that the tool cannot traverse, wherein a distal portion of the flexible guide tube is disposed adjacent a target site in the first configuration;
inform a user that the first configuration includes the one or more sections of the flexible guide tube having the one or more bends that the tool cannot traverse; and command the actuator to move the flexible guide tube to a second configuration, wherein the second configuration does not include the one or more bends that the tool cannot traverse.

2. The system of claim 1, wherein identifying one or more sections of the flexible guide tube having one or more bends that the tool cannot traverse comprises determining whether one or more sections of the flexible guide tube has a radius of curvature smaller than a threshold radius of curvature.

3. The system of claim 1, wherein the flexible guide tube comprises a catheter and the tool comprises a biopsy needle.

4. The system of claim 1, wherein the memory further stores instructions that, when executed by the processor, cause the system to automatically move the flexible guide tube from the first configuration to the second configuration.

5. The system of claim 1, wherein the flexible guide tube comprises a shape sensor.

6. The system of claim 1, wherein the memory further stores instructions that, when executed by the processor, cause the system to command the actuator to return the flexible guide tube to the first configuration after the tool has been inserted into or removed from the flexible guide tube.

7. The system of claim 6, wherein commanding the actuator to return the flexible guide tube to the first configuration is performed in response to manual inputs from the user.

8. The system of claim 7, wherein the memory further stores instructions that, when executed by the processor, cause the system to:
    record shape data indicating a shape of the flexible guide tube in the first configuration; and
    provide at least a portion of the shape data to the user via a display for manually navigating the flexible guide tube along a path indicated by the portion of the shape data.

9. The system of claim 1, wherein the memory further stores instructions that, when executed by the processor, cause the system to command the actuator to move the flexible guide tube into a third configuration after the tool has been inserted into or removed from the flexible guide tube.

10. The system of claim 1, wherein the memory further stores instructions that, when executed by the processor, cause the system to:
    determine, based on the at least one factor, a distance to which the tool should be inserted into the flexible guide tube; and
    convey, via a display, the distance to the user for manually inserting the tool into the flexible guide tube.

11. The system of claim 10, wherein the distance is determined based on a desired stiffness of the flexible guide tube with the tool inserted.

12. The system of claim 1, further comprising the flexible guide tube.

13. A process comprising:
    identifying, based on at least one factor associated with insertion or removal of a tool, one or more sections of a flexible guide tube in a first configuration having one or more bends that the tool would have difficulty traversing while the flexible guide tube is in the first configuration, wherein a distal portion of the flexible guide tube is disposed adjacent a target site in the first configuration;
    informing a user that the first configuration includes the one or more sections of the flexible guide tube having the one or more bends that the tool would have difficulty traversing; and
    moving, via actuation signals sent to an actuator coupled to the flexible guide tube, the flexible guide tube from the first configuration to a second configuration for receiving the tool, wherein the second configuration does not include the one or more bends that the tool would have difficulty traversing.

14. The process of claim 13, wherein identifying the one or more sections comprises determining that a radius of curvature of one or more sections of the flexible guide tube is smaller than a minimum radius of curvature permitted for a portion of the tool.

15. The process of claim 13, wherein identifying the one or more sections comprises determining a shape of the flexible guide tube in the first configuration.

16. The process of claim 15, wherein determining the shape of the flexible guide tube in the first configuration comprises measuring the shape of the flexible guide tube in the first configuration using at least one of a fiber optic shape sensor or a tracked movement of the distal portion of the flexible guide tube.

17. The process of claim 13, wherein a shape of a first portion of the flexible guide tube in the second configuration is substantially the same as a shape of a second portion of the flexible guide tube in the first configuration.

18. The process of claim 13, further comprising returning the flexible guide tube to the first configuration after the tool has been received into the flexible guide tube.

19. The process of claim 18, wherein
    returning the flexible guide tube to the first configuration is performed in response to manual inputs from the user.

20. The process of claim 13, further comprising:
    determining a distance to which the tool should be inserted into the flexible guide tube based on the at least one factor; and
    displaying the distance to the user for manually inserting the tool into the flexible guide tube.

* * * * *

UNITED STATES PATENT AND TRADEMARK OFFICE
CERTIFICATE OF CORRECTION

PATENT NO. : 12,108,997 B2
APPLICATION NO. : 17/165245
DATED : October 8, 2024
INVENTOR(S) : Samuel Kwok Wai Au It is certified that error appears in the above-identified patent and that said Letters Patent is hereby corrected as shown below:

In the Specification

Column 2, Line 8, change "stecrable" to -- steerable --

Column 2, Line 9, change "stecrable" to -- steerable --

Column 2, Line 25, change "stecrable" to -- steerable --

Column 4, Line 5, change "Sec" to -- See --

Column 5, Line 27, change "stecrable" to -- steerable --

Column 5, Line 64, change "Stecrable" to -- Steerable --

Column 6, Line 38, change "stecrable" to -- steerable --

Signed and Sealed this
Third Day of December, 2024

Katherine Kelly Vidal
*Director of the United States Patent and Trademark Office*